United States Patent
Kuroda et al.

(10) Patent No.: US 6,608,235 B1
(45) Date of Patent: Aug. 19, 2003

(54) METHOD OF REDUCING EPOXIDIZED ORGANIC COMPOUND WITH HYDROGEN

(75) Inventors: Nobuyuki Kuroda, Ube (JP); Tokuo Matsuzaki, Ube (JP); Mitsuo Yamanaka, Ube (JP); Takato Nakamura, Ube (JP); Osamu Yamazaki, Ube (JP); Hirofumi Takemoto, Ube (JP)

(73) Assignee: Ube Industries, Ltd., Ube (JP)

( * ) Notice: Subject to any disclaimer, the term of this patent is extended or adjusted under 35 U.S.C. 154(b) by 0 days.

(21) Appl. No.: 09/830,465

(22) PCT Filed: Oct. 27, 1999

(86) PCT No.: PCT/JP99/05949

§ 371 (c)(1),
(2), (4) Date: Aug. 6, 2001

(87) PCT Pub. No.: WO00/26165

PCT Pub. Date: May 11, 2000

(30) Foreign Application Priority Data

Oct. 29, 1998 (JP) .......................... 10-307990

(51) Int. Cl.⁷ .......................... C07C 29/132
(52) U.S. Cl. .............. 568/821; 568/814; 568/826; 568/835; 568/838; 568/867
(58) Field of Search ............. 568/814, 821, 568/835, 867, 826, 838

(56) References Cited

U.S. PATENT DOCUMENTS

| 1,787,205 | A | * | 12/1930 | Loehr |
| 2,524,096 | A | * | 10/1950 | Wood |
| 2,822,403 | A | * | 2/1958 | Hopff |
| 2,997,483 | A | * | 8/1961 | Gray |
| 3,333,010 | A | * | 7/1967 | Urbanek |
| 3,579,593 | A | * | 5/1971 | Wood |
| 3,607,923 | A |   | 9/1971 | Winnick ............ 260/531 R |
| 3,956,405 | A | * | 5/1976 | Katsushima |
| 4,064,186 | A | * | 12/1977 | Gibson |
| 6,166,269 | A | * | 12/2000 | Chaudhari |

FOREIGN PATENT DOCUMENTS

| FR | 2 130 756 A |   | 11/1972 |
| GB | 970790 | * | 9/1964 |
| GB | 1 273 689 A |   | 5/1972 |
| JP | 47-38437 |   | 9/1972 |
| JP | 49-5932 |   | 1/1974 |
| JP | 53-31635 |   | 3/1978 |
| JP | 9-20703 |   | 1/1997 |
| SU | 1657483 A | * | 6/1991 |
| WO | WO 97/38955 |   | 10/1997 |

OTHER PUBLICATIONS

E. Balbolov, et al., Kinetics of Hydrogenation of 1, 2–Epoxycyclododeca–5, 9–diene on Palladium Catalysts, J. Molecular Catalysis, 69, 95–103 (1991) (see p. 3, lines 1–13).

J. P. Varghese, et al., Pd–Catalysed Regiospecific Reduction Ring Opening of Epoxides and Glycidic Esters, Synthetic Comm. 25 (15) 2267–2273 (1995) (see p. 3, line 25 to p. 4, line 2).

Database WPI, Section Ch, Week 199221, Derwent Publications Ltd. London, GB; Class A41, AN 1992–173430; XP002190326 & SU 1 657 483 A (Kuibyshevazot Prodn. Assoc.), Jun. 23, 1991 Abstract.

* cited by examiner

*Primary Examiner*—Michael L. Shippen
(74) *Attorney, Agent, or Firm*—Morgan, Lewis & Bockius LLP

(57) ABSTRACT

In reduction of an epoxy group-containing organic compound, for example, a $C_5$–$C_{20}$ saturated or unsaturated epoxy cycloaliphatic compound, in the presence of a nickel catalyst, by bringing the compound into contact with hydrogen, the target compound can be produced at a high yield by adding a basic substance (for example, an alkali metal hydroxide, an alkali metal carbonate, an alkali metal alkoxide, and an amine compound having 1 to 3 $C_1$–$C_{12}$ alkyl groups), to the reduction reaction system, to thereby restrict production of by-products due to a side deoxidation reaction.

11 Claims, No Drawings

METHOD OF REDUCING EPOXIDIZED ORGANIC COMPOUND WITH HYDROGEN

TECHNICAL FIELD

The present invention relates to a method of reducing an epoxy group-containing organic compound with hydrogen. More particularly, the present invention relates to a method of reducing an epoxy group-containing compound, particularly an epoxy group-containing cycloaliphatic compound, with hydrogen in the presence of a nickel catalyst, with high efficiency, to thereby produce a target compound, particularly a cycloaliphatic saturated alcohol, at high selectivity. The compound, particularly the cycloaliphatic saturated alcohol, produced by the method of the present invention can be converted to, for example, a lactam compound, a lactone compound or a dibasic organic acid, which are useful as materials for producing polyester or polyamide synthetic fibers or resins.

BACKGROUND ART

A cycloaliphatic alcohol, for example, cycloalkanol can be produced by a method in which a cycloalkane corresponding to the alcohol is oxidized with air in the presence of a boric acid catalyst. The conventional air oxidation method is, however, disadvantageous in that since a plurality of types of by-products are produced in a large amount due to successive reactions, and thus the conversion of the cycloalkane must be controlled to a low level, the target cycloalkanol is obtained only in a low yield and the reaction result is unsatisfactory. For example, when cyclododecane is oxidized with air in the presence of a boric acid catalyst, the target cyclododecanol and cyclododecanone are obtained only in a total yield of about 20%. On the other hand, since an epoxycycloalkane and/or an epoxycycloalkene can be produced with a high yield by an epoxidizing reaction of a cycloalkene, if the epoxy compound can be converted to a cycloalkanol with a high efficiency, the cycloalkanol can be produced from the cycloalkene with a high yield.

However, there are few reports concerning the method of converting the epoxycycloalkane and/or epoxycycloalkene to the cycloalkanol.

For example, Japanese Examined Patent Publication No. 47-38, 437 discloses a hydrogenation method in which hydrogen is brought into contact with epoxycyclododecane, to produce cyclododecanol and isomerized cyclododecanone, and in which method, Raney nickel is used as a catalyst.

The Japanese publication, however, does not indicate the yields of the cyclododecanol and cyclododecanone. Therefore, the method of the Japanese publication was carried out by the inventors of the present invention. As a result, it was found that, in the hydrogen-reduction procedure of the epoxycyclododecane compound, a disoxidation reaction of the epoxy group occurred and various hydrocarbons, for example, cyclododecane were produced as by-products in a large amount, and thus the selectivity to the target compounds, namely cyclododecanol and cyclododecanone was unsatisfactory.

Also, Neftekhimiya, 16(1), 114–119, 1976, discloses a method of reducing 1,2-epoxy-5,9-cyclododecadiene with hydrogen by using a nickel catalyst carried on chromium oxide. This method uses a toxic chromium compound and thus is difficult to utilize in practice.

Generally, it is well known that in a hydrogenation reaction of the epoxy compound in the presence of a nickel catalyst, various types of by-product compounds are produced in a large amounts due to disoxidation reaction of the epoxy compound (Tokyo Kagaku-dojin, LECTURE ON ORGANIC REACTION MECHANISM 13, CATALYTIC REACTIONS ((Second Volume), written by Mikio Mitsui).

Further, in J. Mol. Catal., Vol. 69, pages 95–103 (1991), a report concerning hydrogenation of epoxycyclododecadiene is described.

In a reaction example shown in this report, when epoxycyclododecadiene is subjected to a reduction reaction with a hydrogen gas in the presence of a palladium catalyst carried on γ-alumina under a reduced pressure of 1.3 MPa at a reaction temperature of 90° C., cyclododecanol is obtained at a yield of 20%. In the report, a palladium catalyst carried on titania and a palladium catalyst carried on silica were employed. In each case, the yield of the cyclododecanol was less than 20%.

Further, in a Drafted Report, page 68, of the 24th "Progress in Reaction and Synthesis" Sympodium, Nov. 5 to 6, 1998, a hydrogenation reaction of an epoxycyclododecadiene in the presence of a palladium catalyst carried on a carbon material is reported. In this case, the target cyclododecanol was produced at a yield of 5%.

As mentioned above, it is known that the yield of the cyclododecanol by the catalytic hydrogenation reaction of the epoxycyclododecadiene with a hydrogen gas is extremely low.

Furthermore, as an analogous reaction, a method of synthesizing cyclohexanol by a hydrogenation reaction of an epoxycyclohexane is reported in Synthetic Communication, 25(15), p 2267–2273, (1995).

In the method of the publication, it is reported that when an epoxycyclohexane was reduced with ammonium formate ($HCOONH_4$) in the presence of a palladium catalyst carried on activated carbon, the yield of the resultant cyclohexanol was 50%. In this method, however, ammonium formate ($HCOONH_4$) used as a hydrogen-supply source is expensive, the yield of the cyclohexanol obtained by using the expensive hydrogen-supply source is low, and therefore, this method cannot be utilized as a practical method of producing cycloalkanol to be used as a material for producing a lactam.

As mentioned above, a method of producing a hydrogen-reduced compound at a high yield by catalytically reacting an epoxy group-containing organic compound with a hydrogen gas, which is cheap, as a hydrogen-supply source has not yet established, and thus the development of this method is in strongly demand.

DISCLOSURE OF THE INVENTION

An object of the present invention is to provide a method of catalytically reacting an epoxy group-containing organic compound with hydrogen to produce a corresponding hydrogen-reduced compound with a high yield.

A further object of the present invention is to provide a method of catalytically reacting an epoxy group-containing organic compound with hydrogen, while a production of a by-product comprising hydrocarbon compounds due to a disoxidation reaction of the epoxy group-containing organic compound is restricted, to produce a target hydrogen-reduced product at a high yield.

The above-mentioned objects can be attained, by the hydrogen-reduction method of the present invention, for an epoxy group-containing organic compound.

The method of the present invention for reducing an epoxy group-containing organic compound with hydrogen comprises bringing an epoxy group-containing organic compound into contact with hydrogen in the presence of a nickel catalyst, to reduce the epoxy group-containing organic compound in a hydrogen reduction reaction system, in which the reduction reaction system further comprises a basic substance.

In the method of the present invention, the basic substance preferably comprises at least one member selected from the group consisting of hydroxides of alkali metals, carbonates of alkali metals, alkoxides of alkali metals, hydroxides of alkaline earth metals, carbonates of alkaline earth metals, amine compounds having 1 to 3 alkyl groups each having 1 to 12 carbon atoms, and basic oxides of alkaline earth metals and rare earth elements.

In the method of the present invention, the basic substance is preferably present in a total molar amount of 0.01 to 10 times the molar amount of nickel atoms contained in the nickel catalyst.

In the method of the present invention, in the hydrogen reduction reaction system, the basic substance may be carried on the nickel catalyst.

In the method of the present invention, the epoxy group-containing organic compound is preferably selected from epoxy group-containing saturated and unsaturated cycloaliphatic organic compounds having 5 to 20 carbon atoms.

In the method of the present invention, the epoxy group-containing organic compound is selected from the group consisting of, for example, epoxycyclododecane, epoxycyclododecene, epoxycyclododecadiene, epoxycyclohexane, epoxycyclohexene, epoxycyclooctane, and epoxycyclooctene.

BEST MODE FOR CARRYING OUT THE INVENTION

In the method of the present invention in which an epoxy group-containing organic compound is brought into contact with hydrogen in the presence of a nickel catalyst to reduce the compound with hydrogen in a hydrogen reduction reaction system, it is important that the reduction reaction system further comprises a basic material.

The epoxy group-containing organic compound used as a starting compound for the method of the present invention is preferably selected from epoxy group-containing saturated and unsaturated cycloaliphatic organic compounds having 5 to 20 carbon atoms, more preferably 5 to 12 carbon atoms, still more preferably 6 to 12 carbon atoms. The epoxy group-containing cycloaliphatic organic compounds include, for example, epoxycyclododecane, epoxycyclododecene, epoxycyclododecadiene, epoxycyclohexane, epoxycyclohexene, epoxycyclooctane, and epoxycyclooctene. These compounds may have at least one substituent, preferably 1 to 3 substituents, each consisting of an alkyl group, preferably an alkyl group having 1 to 4 carbon atoms. The above-mentioned compound may be employed alone or in a mixture of two or more thereof. Also, these compounds include a plurality of isomers. There is no limitation to the type of the isomers.

The nickel catalyst may be selected from Raney nickel, nickel oxide and stabilized nickel which are effective, as nickel catalysts, for hydrogenation reactions. Particularly the stabilized nickel is preferably employed. The stabilized nickel is advantageous for the method of the present invention in that it is stable and safe in air. The above-mentioned types of nickel catalysts may be employed alone or in a mixture of two or more thereof.

Also, the nickel catalyst may be carried on a carrier comprising at least one member selected from the group consisting of activated carbon, diatomaceous earth and metal oxides.

The above-mentioned materials for the carrier may be employed alone or in a mixture of two or more thereof.

In the method of the present invention, the metal oxides usable as a carrier for the nickel catalyst include alumina, silica, zirconia, titania, zeolite, titanosilicate, magnesia and mixtures thereof. Preferably, alumina, silica, zeolite and mixtures thereof are employed, more preferably, alumina is employed. With respect to the type of alumina usable for the present invention, γ-alumina and α-alumina are usable and, preferably, γ-alumina is employed.

The nickel-carried catalyst usable for the method of the present invention can be prepared by conventional methods. For example, a nickel oxide-carried catalyst is prepared by impregnating a carrier with an aqueous solution of nickel nitrate in a desired amount; evaporating, drying and solidifying the nickel nitrate-impregnated carrier; and calcining the dried nickel nitrite-impregnated carrier. Also, a metal nickel-carried catalyst can be prepared by reducing a nickel oxide-carried catalyst with hydrogen by a conventional method. The amount of nickel contained in the nickel catalyst is preferably 0.1 to 90% by weight, more preferably 5 to 70% by weight, still more preferably 10 to 70% by weight, in terms of metallic nickel, based on the weight of the carrier. When the amount of nickel in the catalyst is less than 0.1% by weight, the resultant catalyst may exhibit an insufficient catalytic activity.

In the nickel catalyst usable for the method of the present invention, the metal oxide usable as a carrier for the catalyst preferably has a specific surface area of 10 $m^2/g$ or more, more preferably 50 to 450 $m^2/g$. The specific surface area can be determined by a nitrogen BET method.

When the nickel catalyst used for the method of the present invention is carried on an alumina carrier, the alumina carrier preferably has a specific surface area of 10 $m^2/g$ or more, more preferably 50 $m^2/g$ or more, still more preferably 80 to 450 $m^2/g$. The above-mentioned alumina may be aluminum oxide prepared by heat-treating aluminum hydroxide. This type of aluminum oxide may be one produced during a procedure for preparing a nickel-carried catalyst by using aluminum hydroxide. The alumina carrier may contain a small amount of Na, Mg, Fe and $SiO_2$. When the content of these impurities is several % or less, they do not impart a great influence on the catalytic performance of the catalyst. When alkali metals and/or alkaline earth metals are contained, they may impart a good effect on the catalytic performance of the catalyst. Also, a composite oxide containing alumina and a metal oxide other than alumina may be used as a carrier for the catalyst for the method of the present invention, as long as the composite oxide has a specific surface area of 10 $m^2/g$ or more.

The amount of nickel carried on the alumina carrier is 0.1 to 90% by weight, preferably 5 to 70% by weight, more preferably 10 to 70% by weight, based on the weight of the alumina carrier. The nickel-carried catalyst may be used without pretreatment, or after a pretreatment, for example, an alkali addition treatment or a hydrogen-reduction treatment.

The nickel catalyst usable for the method of the present invention may be in the form of a powder, or of shaped pellets. Generally, the powder nickel catalyst is used in a liquid phase suspension bed catalytic reaction, and the pellet-shaped catalyst is used in a fixed bed catalytic reaction. In the fixed bed catalytic reaction, a trickle reaction, a liquid phase reaction and a gas phase reaction can each be carried out under certain conditions.

In the case of the powder catalyst usable for the liquid phase suspension bed reaction, the catalyst particles preferably have an average particle size of 5 μm to 300 μm. In the case of the pellet-shaped catalyst usable for the fixed bed catalytic reaction, the pellets preferably have an average length of 1 to 10 mm.

In the method of the present invention, there is no limitation to the amount of the nickel catalyst used for the method. Generally, when a liquid phase suspension bed-type reactor is used, the ratio of the molar amount of nickel atoms contained in the nickel catalyst to the molar amount of the epoxy group-containing organic compound used in the reactor is preferably 1/300,000 or more, more preferably 1/10,000 or more, still more preferably 1/5,000 to 2/1. When the amount of the nickel catalyst is too small, the resultant catalytic effect may be insufficient, when it is too large, the catalytic effect may be saturated, and an economic disadvantage may occur. Also, in the case where the liquid phase suspension bed is employed, a disadvantage, that a load on a stirrer becomes too high, may occur.

In the method of the present invention, a basic substance is contained in the reduction system. The basic substance contained in the reduction reaction system contributes to restricting a disoxidation reaction and to enhancing the yield of the target compound produced by the hydrogen reduction reaction.

The basic substance usable for the method of the present invention preferably comprises at least one member selected from hydroxides of alkali metals, carbonates of alkali metals, alkoxides of alkali metals, hydroxides of alkaline earth metals, carbonates of alkaline earth metals, amine compounds having 1 to 3 alkyl groups each having 1 to 12 carbon atoms, and basic oxides of alkaline earth metals and rare earth elements.

The basic compounds as mentioned above include, for example, hydroxides of alkali metals and alkaline earth metals, for example, sodium hydroxide, lithium hydroxide, potassium hydroxide, barium hydroxide and strontium hydroxide; carbonates of alkali metals and alkaline earth metals, for example, sodium carbonate, potassium carbonate and barium carbonate; alkoxides of alkali metals, for example, sodium methoxide and sodium ethoxide; aliphatic amine compounds, for example, triethylamine, and tributylamine; and basic oxides, for example, magnesium oxide, barium oxide, cerium oxide. Preferably, alkali metal hydroxides and alkali metal alkoxides are employed and more preferably alkali metal hydroxides are employed. These basic compounds may be employed alone or in a mixture of two or more thereof.

In the method of the present invention, the amount of the basic substance is established in response to the molar amount of nickel atoms contained in the nickel catalyst. Preferably the total molar amount of the basic substance is 0.01 to 10 times, more preferably 0.05 to 5 times, still more preferably 0.05 to 1.0 times, further preferably 0.05 to 0.5 times, the molar amount of nickel atoms contained in the nickel catalyst. If the amount of the basic substance is less than 0.01 times in mole, the resultant restricting effect on the disoxidation reaction for the reduction reaction system may be insufficient and the resultant yield of the target compound may be unsatisfactory. Also, if the basic substance is used in an amount more than 10 times in mole, not only the effect of the basic substance may be saturated, and an economical disadvantage occurs but, also, disadvantages such as the catalytic activity significantly decreases, and the amount of by-products generated from the epoxy group-containing organic compound increases, may occur.

In the method of the present invention, the basic substance may be carried on the nickel catalyst. To carry the basic substance on the nickel catalyst, the nickel catalyst may be immersed in an liquid (for example, an aqueous solution or an organic solvent solution) containing the basic substance and dried to produce the nickel catalyst impregnated with the basic substance-containing liquid. In this method, there is no limitation to the immersion temperature. Generally, the immersion is preferably carried out at a temperature of 0 to 100° C., more preferably 0 to 30° C. Also, there is no limitation to the drying conditions. The drying may be carried out in the ambient air atmosphere or an inert gas atmosphere, as long as the drying can be effected uniformly. Preferably, the drying temperature is 60 to 120° C. The solvent for dissolving the basic substance may be selected from a liquid inert to the basic substance, for example, water, ethyl alcohol or a mixture of water with ethyl alcohol.

When, as a basic substance, a basic oxide of an alkaline earth metal is employed, the nickel catalyst is immersed in an aqueous solution of an alkaline earth metal salt in a desired concentration; to this aqueous solution, an aqueous solution containing hydroxyl ions is added to cause a resultant hydroxide of the alkaline earth metal to be precipitated on the nickel catalyst surface; the resultant precipitate is filtered and washed; and the resultant solid is uniformly dried in the ambient air atmosphere or an inert gas atmosphere, or under reduced pressure, to produce a basic substance-carrying nickel catalyst.

Also, when, as a basic substance, a basic oxide of an alkaline earth metal is employed, a nickel catalyst carrying thereon a hydroxide of the alkaline earth metal is uniformly heated in the ambient air atmosphere or an inert gas atmosphere to heat-decompose the alkaline earth metal hydroxide, and to provide a nickel catalyst carrying thereon the basic oxide of the alkaline earth metal.

In the method of the present invention, the basic substance-carrying nickel catalyst is preferably reduced with hydrogen before the catalyst is employed for the hydrogen reduction reaction in accordance with the method of the present invention. The hydrogen reduction pretreatment for the nickel catalyst is preferably carried out at a temperature of 50 to 1000° C., more preferably 70 to 800° C., still more preferably 100 to 700° C. The hydrogen reduction pretreatment may be effected in such a manner that the nickel catalyst is placed in a fixed bed flow type reactor, and a hydrogen gas passes through the reactor, or that the nickel catalyst is placed in an autoclave and dispersed in an inert solvent (for example, normal hexane and cyclohexane) and a hydrogen gas is charged in the autoclave or passed through the dispersion in the autoclave while the dispersion is stirred.

When the catalyst to be subjected to the hydrogen reduction pretreatment is dried, the drying may be effected simultaneously with the reduction in the hydrogen gas atmosphere in accordance with the above mentioned method. However, preferably, the catalyst is preliminarily dried and then subjected to the hydrogen reduction.

The reduction-treated nickel catalyst may be directly used for the reduction reaction. Alternatively, the reduction-treated nickel catalyst may be subjected to a stabilization treatment with an oxygen-containing gas in accordance with a conventional method and then used for the reduction reaction. Also, the catalyst may be shaped in the form of a sphere or a pellet, in response to the type of reactor and the reaction conditions for the reduction reaction of the method of the present invention.

In the method of the present invention, the hydrogen reduction reaction of the epoxy group-containing organic compound may be carried out in an organic solvent or without using the organic solvent. The organic solvent is preferably selected from those which do not affect the the hydrogen reaction in accordance with the method of the present invention, and does not cause production of by-products. The above-mentioned type of organic solvents include, for example, liquid alkanes, for example, n-hexane, n-heptane and cyclohexane; ethers, for example, dimethyl-ether and dixoane; alcohols, for example, propyl alcohol and butyl alcohol; and esters, for example, ethyl acetate and butyl acetate. These organic solvents may be employed alone or in a mixture of two or more thereof. When the reaction solvent is employed, the reaction may be easily controlled. The organic solvent is preferably used in an amount of 100 times or less, more preferably 10 times or less, the weight of the epoxy group-containing organic compound.

The method of the present invention can be carried out by using a batch type reactor or a continuous reaction apparatus, for example, a liquid phase suspension bed type reactor, a fixed bed flowing type reactor or a trickle bed-type rector. In these types of reactors, as mentioned above, the reaction solvent may be employed or not employed.

In the method of the present invention, the starting material containing the epoxy group-containing organic compound may further contain the corresponding reaction products, such as alkanone compound and/or alkanol compound.

In the method of the present invention, the epoxy group-containing organic compound is mixed with a nickel catalyst and a basic substance or a basic substance-carrying nickel catalyst, the mixture is heated under the ambient pressure or a pressure higher than the ambient pressure, optionally while the mixture is stirred, to subject the mixture to a reaction. In this method, the reaction temperature is preferably 80 to 280° C., more preferably 100 to 250° C., still more preferably 100 to 230° C., further preferably 110 to 200° C. Also, in the method of the present invention, the pressure of hydrogen is preferably 98 to 98,000 kPa (1 to 1,000 kg/cm$^2$) more preferably 490 to 39,000 kPa (5 to 400 kg/cm$^2$), still more preferably 980 to 20,000 kPa (10 to 200 kg/cm$^2$).

When the reaction pressure and/or temperature are too low, the hydrogenation reaction for the epoxy groups and the double bonds of the epoxy group-containing organic compound may be insufficiently effected and the target compound may be obtained in an insufficient yield. Also, when the pressure is too high, the hydrogen reduction reaction is sufficiently effected, but the effect of the pressure may be saturated and an economical disadvantage may occur. When the temperature is too high, the amount of by-products, for example, compounds having a high boiling temperature may increase. There is no specific limitation to the reaction time and contact time. Usually, a sufficient reaction time is 3 hours or less.

In the method of the present invention, the reaction products are optionally isolated from the reaction system by, for example, distillation and/or crystallization and are refined.

EXAMPLES

The present invention will be further illustrated by the following examples which are not intended to restrict the scope of the present invention in any way.

Example 1

A stainless steel autoclave having an inner volume of 100 ml and equipped with a stirrer was charged with a stabilized nickel (made by NIKKI KAGAKU K.K., No. 103, nickel content=49 to 52% by weight) which had previously absorbed 0.06 g (1.52 millimoles) of sodium hydroxide, in an amount of 0.89 g (corresponding to 7.60 m moles of nickel atoms), 1.78 g (10.0 m moles of 1,2-epoxy-5,9-cyclododecadiene which will be shown as ECD" hereinafter), and 16 g of cyclohexane, and the inside of the autoclave was pressurized with hydrogen gas, to a pressure of 3,400 kPa (35 kgf/cm$^2$), at room temperature. Then, the autoclave was placed in an oil bath and heated to a temperature of 150° C. After the reaction temperature reached 150° C., the hydrogen gas pressure was increased to 4,900 kPa (50 kgf/cm$^2$), and the reaction mixture was stirred at a constant temperature of 150° C. for one hour. After the reaction was completed, the reaction mixture was cooled to room temperature and the resultant reaction product liquid was subjected to analysis.

The analysis of the reaction product liquid was carried out by a gas chromatography. As a result, it was confirmed that the ECD" was completely consumed, and 9.54m moles of cyclododecanol (which will be shown as CDOL hereinafter), 0.13 m moles of cyclododecanone (which will be shown as CDON hereinafter) and 0.21m moles of cyclododecane (which will be shown as CDAN hereinafter) were produced.

Comparative Example 1

ECD" was subjected to the same hydrogen reduction reaction as in Example 1, except that no sodium hydroxide was absorbed in the nickel catalyst. As a result, ECD"0 was completely consumed. However, it was confirmed that the amount of the resultant CDOL was 8.55 m moles and CDON was produced in an amount of 0.14 m moles and CDAN in 1.22 m moles.

Example 2

The same hydrogen reduction procedure as in Example 1 was carried out, except that, as a nickel catalyst, Raney nickel in an amount of 0.45 g (7.60 m moles) was employed, and an ethyl alcohol solution of 0.06 g (1.52 m moles) of sodium hydroxide was added to the reaction system. As a result, it was confirmed that the ECD" was completely consumed and 8.54 m moles of CDOL, 0.17 m moles of CDON and 0.11 m moles of CDAN were produced.

Comparative Example 2

The same hydrogen reduction procedure as in Example 2 was carried out, except that no ethyl alcohol solution of 0.06 g (1.52 m moles) of sodium hydroxide was added to the reaction system. As a result, it was confirmed that the ECD" was completely consumed and 7.64 m moles of CDOL, 0.14 m moles of CDON and 1.84 m moles of CDAN were produced.

Examples 3 to 10

In each of Examples 3 to 10, the same hydrogen reduction reaction procedure as in Example 1 was carried out with the following exceptions.

The sodium hydroxide in an amount of 0.06 g (1.52 m moles) per 0.89 g (7.60 m moles of nickel atoms) of the stabilized nickel was replaced by the basic compound as shown in Table 1 in the amount as shown in Table 1. The amounts of the resultant CDOL, CDON and CDAN are shown in Table 1.

TABLE 1

| Example No. | Basic substance (Amount) | CDOL (mmol) | CDON (mmol) | CDAN (mmol) |
|---|---|---|---|---|
| 3 | NaOH (0.76 mmol) | 9.46 | 0.12 | 0.31 |
| 4 | NaOMe (1.52 mmol) | 9.54 | 0.15 | 0.20 |
| 5 | $Na_2CO_3$ (1.52 mmol) | 9.07 | 0.16 | 0.70 |
| 6 | LiOH (1.52 mmol) | 9.21 | 0.12 | 0.59 |
| 7 | KOH (0.38 mmol) | 9.18 | 0.16 | 0.43 |
| 8 | $Ba(OH)_2$ (1.52 mmol) | 9.00 | 0.12 | 0.69 |
| 9 | $Sr(OH)_2$ (1.52 mmol) | 8.84 | 0.14 | 0.77 |
| 10 | $Et_3N$ (1.52 mmol) | 8.84 | 0.16 | 0.87 |

Example 11

The same hydrogen reduction procedure as in Example 1 was carried out, with the following exceptions.

The ECD" in an amount of 1.78 g (10.0 m moles) was replaced by epoxycyclododecane (which will be referred to as ECD hereinafter) in an amount of 1.82 g (10.0 m moles). As a result, it was confirmed that the ECD was completely consumed, and the products were 9.23 m moles of CDOL, 0.23 m moles of CDON and 0.05 m moles of CDAN.

It is clear from the comparison of Examples 1 to 11 with Comparative Examples 1 and 2 that by the method of the present invention, the target hydrogenated cyclododecanol and the isomerized cyclododecanone can be produced at a high selectively thereto by contacting the epoxycyclododecane compound with hydrogen, and the production of by-products consisting of hydrocarbons such as cyclododecadiene, cyclododecene and cyclododecane, due to a disoxidation reaction of the epoxy groups, can be restricted.

Example 12

Activated alumina particles having a specific surface area of about 150 $m^2/g$, and usable as a catalyst carrier, in an amount of 5.0 g were immersed in 200 ml of an aqueous solution of 7.44 g of nickel nitrate hexahydrate; the resultant dispersion was heated in a water bath to a temperature of 40° C.; a hot aqueous solution containing 2.04 g of sodium hydroxide in an amount of 100 ml was mixed at a temperature of 40° C. into the hot dispersion; and the resultant mixture was fully stirred and then left to stand at a temperature of 40° C. for 2 hours. The resultant precipitate in the mixture was collected by a suction filtration using a Nutsche funnel and a filter paper sheet, and repeatedly washed with pure water in a total amount of about 500 ml to an extent such that the pH value of the filtrate reached 8.0 or less.

The obtained solid product was simultaneously dried and pulverized at a temperature of 120° C. Then, the pulverized product was subjected to a calcination in an electric furnace at a temperature of 500° C. for 3 hours in the ambient air atmosphere. The calcined product was placed in a fixed bed flowing type reactor made of quartz, and subjected to a reduction reaction at a temperature of 500° C. for one hour in a hydrogen gas stream at a flow rate of 40 ml/min.; and the reduced product was cooled to room temperature and then subjected to a stabilization treatment with a nitrogen gas containing a diluted oxygen gas in an amount of 3%, to provide a nickel catalyst in which 30% by weight of nickel are carried on the activated alumina carrier.

The resultant nickel catalyst in an amount of 1.50 g was placed in a stainless steel autoclave (having a capacity of 120 ml), and mixed with 20 ml of cyclohexane. The autoclave was filled by a hydrogen gas under a pressure of 5,100 kPa (50 atmospheres) at room temperature, and the mixture in the autoclave was subjected to a provisional reduction treatment at a temperature of 230° C. for one hour and then cooled. Thereafter, 8.92 g (50 m moles) of ECD" and 7 ml of cyclohexane were fed into the autoclave, and the resultant reaction mixture was subjected to a hydrogen reduction reaction at a temperature of 150° C. for one hour while the partial pressure of hydrogen in the reaction system is maintained constant at 5066.25 kPa (50 atmospheres).

After the reaction was completed, the reaction product mixture was filtered and the filtrate was analyzed by a gas chromatography. In the result, it was confirmed that the starting material ECD" was completely consumed, and 8.04 g (43.7 m moles) of CDOL and 0.04 g (0.2 m moles) of CDON were produced. No ECD was found as a by-product. It was found that 0.93 g (5.6 m moles) of CDAN were produced as a by-product due to a deoxidation reaction.

Example 13

ECD" was reduced with hydrogen by the same procedure as in Example 12, with the following exceptions.

Alumina having a specific surface area of about 200 $m^2/g$ was employed as a catalyst carrier.

In the reaction result, the starting material ECD" was completely consumed, and 8.16 g (44.3 m moles) of CDOL and 0.05 g (0.3 m moles) of CDON were produced. Also, as by-products, 0.00 g (0.0 m mole) of ECD and 0.85 g (5.1 m moles) of CDAN were produced.

Example 14

ECD" was reduced with hydrogen by the same procedure as in Example 12, with the following exceptions.

Alumina having a specific surface area of about 8 $m^2/g$ was employed as a catalyst carrier.

In the reaction, the starting material ECD" was completely consumed, and 7.09 g (38.5 m moles) of CDOL and 0.18 g (1.0 m mole) of CDON were produced. Also, as by-products, 0.00 g (0.0 m mole) of ECD and 1.72 g (10.2 m moles) of CDAN were produced.

Example 15

ECD" was reduced with hydrogen by the same procedure as in Example 12, with the following exceptions.

A silica gel having a specific surface area of about 440 $m^2/g$ was employed as a catalyst carrier in place of the activated alumina.

In the reaction, the starting material ECD" was completely consumed, and 7.69 g (41.8 m moles) of CDOL and 0.08 g (0.5 m moles) of CDON were produced. Also, as by-products, 0.00g (0.0 m mole) of ECD and 1.19 g (7.1 m moles) of CDAN were produced.

Example 16

The same nickel catalyst as in Example 12 was immersed in an amount of 1.5 g in 10 ml of an aqueous solution containing sodium hydroxide in an amount corresponding to 0.2 equivalent based on the amount of metallic nickel contained in the catalyst, and the alkali solution-carrying catalyst was dried at a temperature of 120° C. and pulverized to provide a alkali-carrying nickel catalyst.

The catalyst was placed in a fixed bed flowing type reactor made from quartz and subjected to a reduction treatment at a temperature of 500° C. for one hour in a hydrogen gas stream at a flow rate of 40 ml/min., the reduction-treated catalyst was cooled to room temperature and then subjected to a stabilization treatment with a nitrogen gas containing diluted oxygen in an amount of 3%.

The pre-treated nickel catalyst in an amount of 1.50 g was placed in a stainless steel autoclave (having a capacity of 120 ml), and mixed with 20 ml of cyclohexane. The autoclave was filled by a hydrogen gas under a pressure of 5100 kPa (50 atmospheres) at room temperature.

The reaction mixture in the autoclave was subjected to a previous reduction treatment at a temperature of 230° C. for one hour, and then cooled. The reaction mixture was mixed with 8.92 g (50 m moles) of ECD" and 7 ml of cyclohexane, and the resultant reaction system was subjected to a hydrogen reduction reaction at a temperature of 150° C. for one hour while the partial pressure of hydrogen in the autoclave was maintained constant at 5066.25 kPa (50 atmospheres).

After the reaction was completed, the resultant reaction mixture was filtered, and the filtrate was subjected to a gas chromatographic analysis. As a result of the analysis, it was confirmed that the starting material ECD" was completely consumed, 8.85 g (48.0 m moles) of CDOL and 0.02 g (0.1 m mole) of CDON were obtained and as by-products, 0.00 g (0.0 m mole) of ECD and 0.28 g (1.7 m moles) of CDAN were produced.

Example 17

The same hydrogen reduction of ECD as in Example 12 was carried out, with the following exceptions.

The catalyst carrier was prepared by the following procedures.

An alumina powder usable as a catalyst carrier in an amount of 5.0 g was immersed in 200 ml of an aqueous solution containing 2.51 g of magnesium nitrate hexahydrate, the mixture was heated to a temperature of 40° C. in a water bath and mixed with 100 ml of a hot aqueous solution (40° C.) containing 0.79 g of sodium hydroxide; then the mixture was fully stirred and then left to stand at 40° C. for 2 hours.

The resultant precipitate in the mixture was collected by a suction filtration using a Nutsche funnel and a filter paper sheet, and repeatedly washed with pure water in a total amount of about 500 ml to an extent such that the pH value of the filtrate reached 8.0 or less.

The obtained solid product was simultaneously dried and pulverized at a temperature of 120° C. Then, the pulverized product was subjected to a calcination in an electric furnace at a temperature of 500° C. for 3 hours in the ambient air atmosphere. A magnesium oxide-containing alumina complex oxide having a specific surface area of about 100 m$^2$/g and usable as a catalyst carrier was obtained.

In the same procedures as in Example 16, reduced nickel in an amount of 30% by weight was carried on the above-mentioned carrier, and the resultant catalyst was subjected to a stabilization treatment.

A hydrogen reduction was applied to ECD" by the same procedures, as in Example 16, except that the catalyst of Example 16 was replaced by the pre-treated catalyst mentioned above in an amount of 1.50 g.

As an analysis result, it was confirmed that the starting material ECD" was completely consumed, and 8.32 g (45.2 m moles) of CDOL and 0.03 g (0.2 m moles) of CDON were obtained, and as by-products, 0.00 g (0.0 m mole) of ECD and 0.73 g (4.4 m moles) of CDAN were produced.

Example 18

ECD" was reduced with hydrogen by the same procedure as in Example 12, with the following exceptions.

The reduction reaction temperature was changed to 140° C.

In the reaction result, the starting material ECD" was completely consumed, and 8.70 g (47.2 m moles) of CDOL and 0.00 g (0.0 m mole) of CDON were obtained. Also, as by-products, 0.09 g (0.5 m mole) of ECD and 0.34 g (2.0 m moles) of CDAN were produced.

Examples 19 to 20

(Catalyst Life)

In each of Examples 19 to 22, ECD was reduced with hydrogen by the same procedures as in Example 16, with the following exceptions.

The hydrogen reduction reaction was repeated plural times in the same manner as in Example 16, while the used catalyst was recovered and re-used in the next reaction procedure.

In each time of the reaction, the resultant product was analyzed. The amounts in m moles of the products are shown in Table 2.

TABLE 2

| Example No. | 16 | 19 | 20 | 21 | 22 |
|---|---|---|---|---|---|
| Reaction Times | 1 | 2 | 3 | 4 | 5 |
| CDAN | 1.7 | 1.3 | 1.5 | 1.2 | 1.4 |
| ECD | 0.0 | 0.0 | 0.3 | 0.4 | 0.4 |
| CDON | 0.1 | 0.1 | 0.0 | 0.0 | 0.3 |
| CDOL | 48.0 | 48.3 | 48.0 | 48.2 | 47.7 |

(The amount of each product is in the units of millimole)

Examples 23 to 25

(Catalyst Life)

In each of Examples 23 to 25, ECD was reduced with hydrogen by the same procedures as in Example 15, with the following exceptions.

The hydrogen reduction reaction was repeated plural times in the same manner as in Example 15, while the used catalyst was recovered and re-used in the next reaction procedure.

In each time of the reaction, the resultant product was analyzed. The amounts in m moles of the products are shown in Table 3.

TABLE 3

| Example No. | 15 | 23 | 24 | 25 |
|---|---|---|---|---|
| Reaction Times | 1 | 2 | 3 | 4 |
| CDAN | 7.1 | 11.5 | 8.3 | 6.9 |
| ECD | 0.0 | 5.9 | 17.4 | 23.5 |
| CDON | 0.5 | 1.4 | 2.4 | 2.4 |
| CDOL | 41.8 | 30.6 | 21.1 | 16.4 |

(The amount of each product is in the units of millimole

As mentioned above, the method by which a cycloalkanol can be prepared from an epoxide of a cyclohydrocarbon with a high yield has not been known before the present invention. However, as clearly shown in Examples 12 to 25, it was confirmed that the method of the present invention enables a cycloalkanol to be produced at a high yield in the presence of an alumina-carrying nickel catalyst under conditions of a hydrogen pressure of 98 to 98,000 kPa (1 to 1000 kg/cm$^2$) and a reaction temperature of 100 to 280° C. Thus it is possible to prepare a cycloalkanol from a cycloolefin compound through an epoxide thereof at a high efficiency and to obtain a relatively cheap lactam material.

Example 26

An activated alumina powder for catalyst carrier having a specific surface area of 150 m²/g in an amount of 5.0 g was immersed in 200 ml of an aqueous solution containing 7.44 g of nickel nitrate hexahydrate, the resultant dispersion was heated to a temperature of 40° C. by using a water bath, and, into the heated dispersion, 100 ml of a hot aqueous solution (40° C.) containing 2.04 g of sodium hydroxide were mixed and the resultant mixture was fully stirred and left to stand at 40° C. for 2 hours.

The resultant precipitate in the mixture was collected by a suction filtration using a Nutsche funnel and a filter paper sheet, and repeatedly washed with pure water in a total amount of about 500 ml to an extent such that the pH value of the filtrate reached 8.0 or less.

The obtained solid product was simultaneously dried and pulverized at a temperature of 120° C. Then, the pulverized product was subjected to a calcination in an electric furnace at a temperature of 500° C. for 3 hours in the ambient air atmosphere. The calcined product was placed in a fixed bed flowing type reactor made from quartz, and subjected to a reduction reaction at a temperature of 500° C. for one hour in a hydrogen gas stream at a flow rate of 40 ml/min.; and the reduced product was cooled to room temperature and then subjected to a stabilization treatment with a nitrogen gas containing a diluted oxygen gas in an amount of 3%, to provide a nickel catalyst in which 30% by weight of nickel are carried on the carrier. The nickel catalyst was subjected to the following pre-treatment and then used for the reaction mentioned below.

The nickel catalyst was immersed in 100 ml of an aqueous solution containing sodium hydroxide in an amount (0.204 g) corresponding to 0.2 equivalent based on the amount of the metallic nickel contained in the catalyst, the alkali solution-carrying nickel catalyst was dried and pulverized at 120° C. to provide an alkali-carrying nickel catalyst.

The catalyst was placed in a fixed bed flowing type reactor made from quartz and subjected to a reduction treatment in a hydrogen gas stream at a flow rate of 40 ml/min. at 500° C. for one hour, then cooled to room temperature. The cooled catalyst was subjected to a stabilization treatment with a nitrogen gas containing diluted oxygen in an amount of 3%.

The pre-treated catalyst in an amount of 1.50 g was placed in a stainless steel autoclave (having a capacity of 120 ml), and mixed with 20 ml of cyclohexane. The autoclave was filled with hydrogen gas under a pressure of 5,100 kPa (50 atmospheres) at room temperature, and the mixture in the autoclave was subjected to a provisional reduction treatment at a temperature of 230° C. for one hour and then cooled. Thereafter, 8.92 g (50 m moles) of ECD" and 7 ml of cyclohexane were fed into the autoclave, and the resultant reaction mixture was subjected to a hydrogen reduction reaction at a temperature of 150° C. for one hour while the partial pressure of hydrogen in the reaction system is maintained constant at 5066.25 kPa (50 atmospheres).

After the reaction was completed, the reaction product mixture was filtered and the filtrate was analyzed by gas chromatography. In the result, it was confirmed that the starting material ECD" was completely consumed, and 8.85 g (48.0 m moles) of CDOL and 0.02 g (0.1 m moles) of CDON were obtained. No ECD was found as a by-product.

It was found that 0.28 g (1.7 m moles) of CDAN were produced as a by-product due to a disoxidation reaction. Namely, the amount of the by-products was only 1.7 m moles.

Example 27

ECD" was reduced with hydrogen by the same procedure as in Example 26, with the following exceptions.

A catalyst carrier was prepared by the following procedures.

The same activated alumina powder as in Example 27 in an amount of 5.0 g was immersed in 200 ml of an aqueous solution containing 2.51 g of magnesium nitrate hexahydrate, the resultant dispersion was heated in a water bath to a temperature of 40° C.; 100 ml of a hot aqueous solution containing 0.79 g of sodium hydroxide were mixed at a temperature of 40° C. into the hot dispersion; and the resultant mixture was fully stirred and then left to stand at a temperature of 40° C. for 2 hours. The resultant precipitate in the mixture was collected by a suctional filtration using a Nutsche funnel and a filter paper sheet, and repeatedly washed with pure water (in a total amount of about 500 ml) to an extent such that the pH value of the filtrate reached 8.0 or less.

The obtained solid product was simultaneously dried and pulverized at a temperature of 120° C. Then, the pulverized product was subjected to a calcination in an electric furnace at a temperature of 500° C. for 3 hours in the ambient air atmosphere, to obtain a $Al_2O_3$—MgO mixture as a carrier.

By the same procedures as in Example 26, the carrier carried thereon 30% by weight of reduced nickel, and the resultant reduced nickel catalyst was subjected to the stabilization treatment.

The same hydrogen reduction procedure for ECD" as in Example 26 was carried out, except that the pre-treated catalyst was employed in an amount of 1.50 g.

In the result, the starting material ECD" was completely consumed, and 8.32 g (45.2 m moles) of CDOL and 0.03 g (0.2 m moles) of CDON were obtained.

The by-product included 0.00 g (0.0 m mole) of ECD and 0.73 g (4.4 m moles) of CDAN. Namely, the resultant by-product was in an amount of 4.4 m moles.

Example 28

ECD" was reduced with hydrogen by the same procedure as in Example 26, with the following exceptions.

The hydrogen reduction temperature was set to 140° C.

In the reaction result, the starting material ECD" was completely consumed, and 8.70 g (47.2 m moles) of CDOL and 0.00 g (0.0 m moles) of CDON were obtained. Also, as by-products, 0.09 g (0.5 m mole) of ECD and 0.34 g (2.0 m moles) of CDAN were produced. Namely, the by-product was produced in an amount of 2.5 m moles.

Comparative Example 3

ECD" was reduced with hydrogen by the same procedure as in Example 26, with the following exceptions.

No alkali treatment was applied to the catalyst.

In the reaction result, the starting material ECD" was completely consumed, and 8.04 g (43.6 m moles) of CDOL and 0.03 g (0.2 m moles) of CDON were produced. Also, as by-products, 0.00 g (0.0 m mole) of ECD and 0.98 g (5.9 m moles) of CDAN were produced. Namely, the amount of the by-product was 5.9 m moles.

Example 29

ECD" was reduced with hydrogen by the same procedure as in Example 26, with the following exceptions.

The reduction treatment for the alkali-treated catalyst was omitted.

In the reaction result, the starting material ECD" was completely consumed, and 8.45 g (45.9 m moles) of CDOL and 0.06 g (0.4 m moles) of CDON were obtained. Also, as by-products, 0.17 g (1.0 m mole) of ECD and 0.54 g (3.2 m moles) of CDAN were produced. Namely, the amount of the by-product was 4.2 m moles.

Examples 30 to 34
(Catalyst Life)

A batch reaction for 50 millimoles of a starting material ECD" using the 30 weight % nickel-carrying catalyst prepared by the same procedures as in Example 26 was repeated plural times under the same reaction conditions as in Example 26. The product obtained in each time of reaction was analyzed. The amounts in millimoles of the products are shown in Table 4.

TABLE 4

| Example No. | 30 | 31 | 32 | 33 | 34 |
|---|---|---|---|---|---|
| Pretreatment of catalyst | Alkali treatment and reduction treatment | | | | |
| The number of times of reaction | 1 | 2 | 3 | 4 | 5 |
| CDAN | 1.7 | 1.3 | 1.5 | 1.2 | 1.4 |
| ECD | 0.0 | 0.0 | 0.3 | 0.4 | 0.4 |
| CDON | 0.1 | 0.1 | 0.0 | 0.0 | 0.3 |
| CDOL | 48.0 | 48.3 | 48.0 | 48.2 | 47.7 |

(The amounts of products are in the units of millimoles.)

Comparative Examples 4 to 7
(Catalyst Life)

In each of Comparative Examples 4 to 7, the batch reaction under the same reaction conditions as in Comparative Example 3 was repeated at the number of times shown in Table 5.

TABLE 5

| Comparative Example No. | 4 | 5 | 6 | 7 |
|---|---|---|---|---|
| Pretreatment of catalyst | No alkali-treatment, only reduction treatment | | | |
| The number of times of reaction | 1 | 2 | 3 | 4 |
| CDAN | 5.1 | 6.9 | 7.2 | 11.7 |
| ECD | 0.0 | 0.0 | 0.0 | 0.0 |
| CDON | 0.2 | 0.2 | 0.5 | 0.4 |
| CDOL | 44.2 | 42.2 | 42.0 | 37.5 |

(The amounts of products are in the units of millimoles.)

As Examples 26 to 34 clearly show, the method of the present invention in which an epoxy group-containing organic compound is reduced with hydrogen to produce a corresponding hydrogenated product, by using a nickel catalyst alkali-treated and then reduction treated with hydrogen, can enhance the hydrogen reduction activity of the organic compound and the selectivity to the corresponding hydrogenated product and improve the catalyst life.

What is claimed is:

1. A method of reducing an epoxy group-containing organic compound with hydrogen, comprising contacting a nickel catalyst and a basic substance to form a basic substance-carrying nickel catalyst, pretreating the basic substance-carrying nickel catalyst with hydrogen, and bringing an epoxy group-containing saturated or unsaturated cycloaliphatic organic compound having 5 to 20 carbon atoms into contact with hydrogen in the presence of the basic substance-carrying nickel catalyst, to reduce the epoxy group-containing saturated or unsaturated cycloaliphatic organic compound in a hydrogen reduction reaction system.

2. The method as claimed in claim 1, wherein the basic substance comprises at least one member selected from the group consisting of hydroxides of alkali metals, carbonates of alkali metals, alkoxides of alkali metals, hydroxides of alkaline earth metals, carbonates of alkaline earth metals, amine compounds having 1 to 3 alkyl groups each having 1 to 12 carbon atoms, and basic oxides of alkaline earth metals and rare earth elements.

3. The method as claimed in claim 1, wherein the basic substance is present in a total molar amount of 0.01 to 10 times the molar amount of nickel atoms contained in the nickel catalyst.

4. The method as claimed in claim 1, wherein the step of contacting the nickel catalyst and the basic substance is performed by impregnating the nickel catalyst with a liquid containing the basic substance and then drying.

5. The method as claimed in claim 1, wherein the nickel catalyst comprises at least one member selected from the group consisting of Raney nickel, nickel oxide and stabilized nickel.

6. The method as claimed in claim 1, wherein the nickel catalyst is carried on a carrier comprising at least one member selected from the group consisting of activated carbon, metal oxides and diatomaceous earth.

7. The method as claimed in claim 6, wherein the metal oxides used as the carrier for the nickel catalyst comprises at least one member selected from the group consisting of alumina, silica, zirconia, titania, zeolite, titanosilicate and magnesia.

8. The method as claimed in claim 6, wherein the metal oxides used as the carrier for the nickel catalyst have a specific surface area of 10 $m^2/g$ or more.

9. The method as claimed in claim 7, wherein the alumina used as the carrier for the nickel catalyst has a specific surface area of 10 $m^2/g$ or more.

10. The method as claimed in claim 1, wherein the epoxy group-containing saturated or unsaturated cycloaliphatic organic compound is selected from the group consisting of epoxycyclododecane, epoxycyclododecene, epoxycyclododecadiene, epoxycyclohexane, epoxycyclohexene, epoxycyclooctane, and epoxycyclooctene.

11. The method as claimed in claim 1, wherein the step of pretreating the basic substance-carrying nickel catalyst with hydrogen is carried out at a temperature of 50–1000° C.

* * * * *